United States Patent [19]
Martin et al.

[11] Patent Number: 5,968,482
[45] Date of Patent: Oct. 19, 1999

[54] α-HYDROXYKETOALKYL DERIVATIVES AS LIGHT PROTECTION FILTERS

[75] Inventors: Roland Martin, Weinheim; Ingeborg Stein, Erzhausen; Ulrich Heywang, Darmstadt; Michael Schwarz, Gross-Gerau; Thekla Kurz, Gross-Gerau, all of Germany

[73] Assignee: Merck Patent Gesellschaft MIT Beschrankter Haftung, Germany

[21] Appl. No.: 08/710,767

[22] Filed: Sep. 20, 1996

Related U.S. Application Data

[62] Division of application No. 08/137,014, Oct. 15, 1993, Pat. No. 5,600,007, which is a continuation of application No. PCT/EP93/00245, Feb. 3, 1993.

[30] Foreign Application Priority Data

Feb. 15, 1992 [DE] Germany .................... 42 04 651

[51] Int. Cl.⁶ ................ A61K 7/42; A01N 43/66; C07C 49/00; C07D 251/00
[52] U.S. Cl. ............... 424/59; 424/78; 514/387; 514/545; 514/570; 514/681; 514/685; 514/844; 544/180; 544/194; 544/204; 544/208; 544/209; 544/211; 544/212; 544/219; 544/220; 544/223; 544/349; 548/304.4; 548/306.4; 560/51; 560/53; 568/303; 568/306; 568/308; 568/325; 568/326; 568/327; 568/331; 568/373; 568/376

[58] Field of Search ................ 568/306, 373, 568/376, 303, 308, 325, 326, 327, 331; 560/51, 53; 544/180, 194, 204, 208, 209, 211, 212, 219, 220, 223, 349; 562/465; 548/304.4, 306.4, 310.1; 514/844, 545, 570, 685, 681, 241, 244, 249, 387; 424/59, 78.02

[56] References Cited

U.S. PATENT DOCUMENTS 3,920,668  11/1975  Nicki et al. .............. 508/306
5,232,688  8/1993  Ziegler et al. .
5,600,007  2/1997  Martin et al. ............ 508/306

*Primary Examiner*—John Kight
*Assistant Examiner*—Raymond Covington
*Attorney, Agent, or Firm*—Miller, White, Zelano, & Branigan, P.C.

[57] ABSTRACT

The invention relates to the use of α-hydroxyketoalkyl derivatives as light protection filters for cosmetic or pharmaceutical products, the α-hydroxyketoalkyl group being linked, if appropriate via a spacer, to a chromophoric group which has an absorption maximum in a wavelength range of between 280 and 400 nm and has a conjugated π-electron system of at least 8 π-electrons, and to new α-hydroxyalkyl derivatives, processes for their preparation and pharmaceutical and cosmetic formulations comprising these derivatives as light protection substances.

5 Claims, No Drawings

α-HYDROXYKETOALKYL DERIVATIVES AS LIGHT PROTECTION FILTERS

This is a division of the application Ser. No. 08/137.014 filed Oct. 15, 1993 now U.S. Pat. No. 5,600,007 which is a continuation of PCT/EP93/00245 filed Feb. 3, 1993.

The invention relates to the use of α-hydroxyketoalkyl derivatives as light protection filters for cosmetic or pharmaceutical products, the α-hydroxyketoalkyl group being linked, if appropriate via a spacer, to a chromophoric group which has an absorption maximum in a wavelength range of between 280 and 400 nm and has a conjugated π-electron system of at least 8 π-electrons, and to new α-hydroxyketoalkyl derivatives, processes for their preparation and their use in cosmetic formulations, in particular for protection from solar radiation, and in pharmaceutical formulations for preventive treatment of inflammations and allergies of the skin or certain types of cancer.

As is known, the skin is sensitive to solar rays, which can cause common sunburn or erythema, but also burns of a greater or lesser degree.

However, solar rays also have other negative actions: they cause the skin to lose its elasticity and develop wrinkles, and therefore lead to premature aging. Dermatoses can also sometimes be observed. In the extreme case, skin cancer occurs in some humans.

It is also desirable to protect hair from photo-chemical damage, in order to prevent changes in color shades, bleaching or damage of a mechanical nature.

It is known that the components contained in cosmetic preparations are not always sufficiently stable to light and decompose under the action of light rays.

As is known, the most dangerous part of solar rays comprises the ultraviolet rays having a wavelength of less than 400 nm. It is also known that due to the presence of the ozone layer of the earth's atmosphere, which absorbs some of the solar radiation, the lower limit of ultraviolet rays which reach the earth's surface is at about 280 nm.

It therefore seems desirable to provide compounds which absorb UV rays in a wavelength range from 280 to 400 nm, that is to say also UV-B rays having a wavelength of between 280 and 320 nm, which play a decisive role in the development of solar erythema, and also UV-A rays having a wavelength of between 320 and 400 nm, which tan but also age the skin, promote initiation of an erythematous reaction or increase this reaction in certain people or can even trigger off phototoxic or photoallergic reactions.

The sunscreen filters customary at present in cosmetics are divided into UVA and UVB filters. While there are good filters in the UVB range (280–320 nm), with substances such as Eusolex® 6300 or Eusolex® 232, those in the UVA range (320–400 nm) present problems:

Dibenzoylmethanes, such as Parsol® 1789 or Eusolex® 8020 do not have an unlimited stability under UV irradiation, which on the one hand reduces the filtering effectiveness with time and on the other hand can promote photosensitizations of the skin in isolated cases. The benzophenones also used as UVA filters have only a limited solubility in the oils used in cosmetics, and they have a relatively low absorption. On the other hand, only few water-soluble UVA filters are currently known, but their UV absorption is low.

Similar benzylidenecamphor derivatives are known from EP 03 90 682. However, these have at least one hydroxyl group on the phenylene ring. Although these compounds can also be used as UV filters in sunscreen agents, they are more suitable as antioxidants because of the phenolic hydroxyl group. These compounds furthermore have only a limited solubility in conventional carriers for cosmetics, in particular in aqueous suspensions, so that in sunscreen agents, they usually have to be employed together with other UV filters.

The conventional light protection filters as a rule have a low or inadequate adhesion to the skin, which leads to a relatively short duration of the protective action of the filter and in particular to virtually complete removal of the filter during bathing.

It has been found that certain α-hydroxyketoalkyl derivatives, in particular 4-(1-oxo-2-hydroxyethyl)phenyl derivatives, have outstanding UVB filter properties. Their solubility in the oils used in cosmetics is very good, so that use concentrations of up to at least 10% of the formulation, even in complicated formulations, are possible. The corresponding sulfonic acids are a water-soluble form of the new filter. The water-solubility here is so good that use concentrations of 10% are likewise possible.

The α-hydroxyketoalkyl derivatives furthermore have an excellent adhesion to skin, and in some cases a self-tanning effect, like, for example, other hydroxyketo compounds (dihydroxyacetone).

The compounds according to the invention furthermore have an exceptional photostability to UV radiation, which by far exceeds the stability of UV filter substances known to date.

If the extinction has a minimum in the UVA range, this is not a disadvantage, since a UVA filter can be incorporated into the formulation without problems.

The compounds of the formula I furthermore can also be used for preventive treatment of inflammations and allergies of the skin and for prevention of certain types of cancer.

In addition to their good properties as filters, the compounds according to the invention are distinguished by a good heat and photochemical stability.

These compounds furthermore offer the advantage of not being toxic or irritating and of being completely harmless to the skin.

They are distributed uniformly in the conventional carriers for cosmetics, and in particular can form a continuous film in fatty carriers; they can be applied to the skin in this manner in order to form an effective protective film.

The invention relates to the use of α-hydroxyketoalkyl derivatives as light protection filters for cosmetic or pharmaceutical products, the α-hydroxyketoalkyl group being linked, if appropriate by a spacer, with a chromophoric group which has an absorption maximum in a wavelength range of between 280 and 400 nm and has a conjugated π-electron system of at least 8 π-electrons.

The invention furthermore relates to α-hydroxyketoalkyl derivatives of the formula I

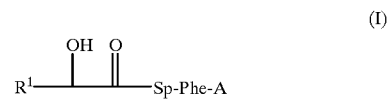

(I)

wherein

R$^1$ is H or alkyl having 1 to 10 C atoms,

Sp is $(CH_2)_n$ or —CH=CH—, n is 0 or an integer between 1 and 10,

Phe is phenylene which is unsubstituted or substituted by 1 to 4 hydroxyl, alkyl or alkyloxy groups, the alkyl groups in each case having 1–10 C atoms, and A is a substituent group which has a total of up to 60 carbon, sulfur, nitrogen and oxygen atoms in the basic structure and contains a conjugated π-electron system of at least 4 π-electrons in conjugation with the Phe group.

The substituent group A has a 4 π-electron system, which is optionally bonded in an aromatic or heteroaromatic ring system, and as a rule contains 1 to 4 oxygen or nitrogen atoms and comprises basic structures which cause or have UV filter properties in accordance with the prior art; the substituent group A is preferably a radical chosen from the formulae (a) to (g)

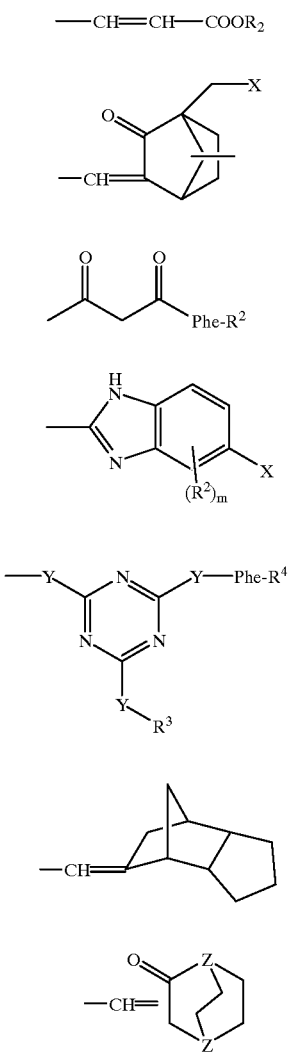

wherein, in each case independently of one another,
R² has one of the meanings given for R¹,
Phe has the meaning given,
X is H, R² or SO₃H,
m is 0, 1, 2 or 3,
Y in each case independently of one another is 0 (sic) or NH,
z in each case independently of one another is CH or N and
R³ has one of the meanings of R¹ or is Phe-R⁴, wherein R⁴ is a radical chosen from the formulae (a), (b), (d), (f) and (g).

In these formulae, R¹ and R² are hydrogen or straight-chain or branched alkyl, preferably a methyl, ethyl, n-propyl, i-propyl, n-butyl, i-butyl, t-butyl or 1,1,3,3-tetramethylbutyl radical or hydrogen, in particular hydrogen.

The phenylene group (Phe) is preferably a 1,4-phenylene group which is unsubstituted or substituted by one to four alkyl or alkoxy groups.

The phenylene group (Phe) is preferably unsubstituted or substituted by one or two alkoxy groups having 1 to 8 C atoms, in particular by methoxy, ethoxy or 2-ethylhexyloxy groups.

Preferred compounds of the formula I are those of the formulae I1 to I8, wherein A has the meaning given and R⁷ is alkyl or alkoxy having 1 to 10 C atoms and n is 1 or 2.

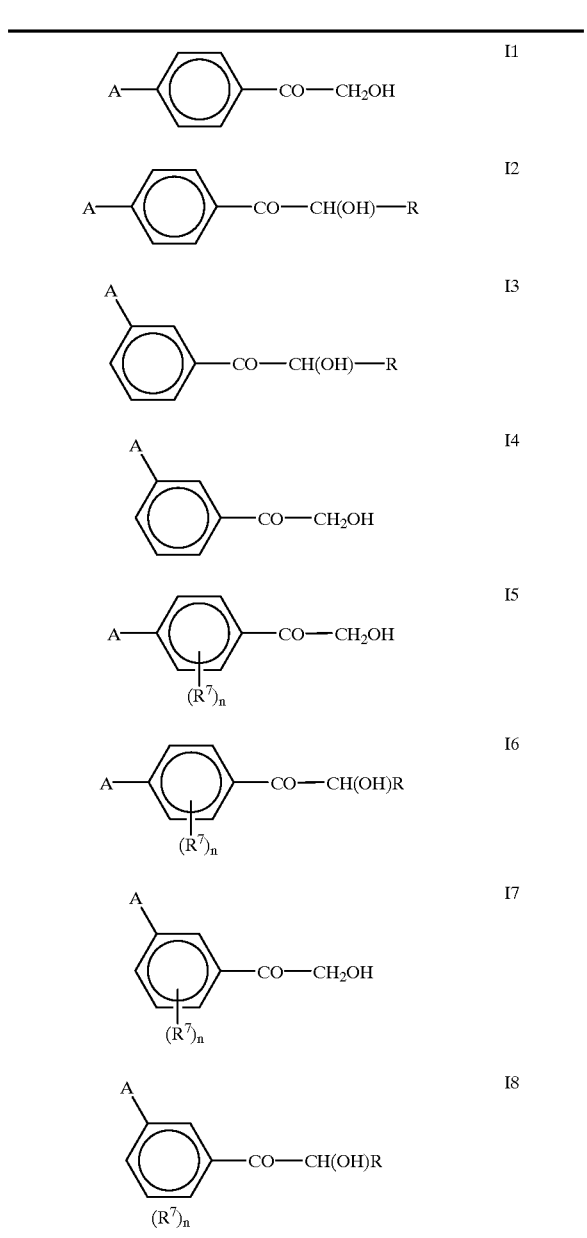

Other preferred embodiments are:
a) α-hydroxyketoalkyl derivatives wherein Phe is unsubstituted 1,4-phenylene;
b) α-hydroxyketoalkyl derivatives wherein n is 0;
c) α-hydroxyketoalkyl derivatives wherein R¹ is H;

d) α-hydroxyketoalkyl derivatives of the formula Ia

(Ia)

e) α-hydroxyketoalkyl derivatives of the formula Ib

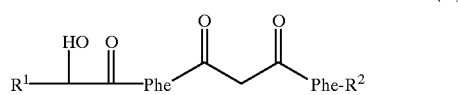
(Ib)

f) α-hydroxyketoalkyl derivatives of the formula Ic

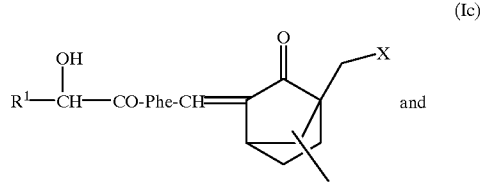
and
(Ic)

g) α-hydroxyketoalkyl derivatives wherein Phe is an unsubstituted 1,4-phenylene group and $R^1$ is H.

The compounds of the formula I are obtained, for example, by a process in which a formylbenzylidene derivative of the formula II

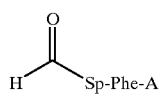
(II)

wherein Phe, Sp and A have the meaning given, is reacted with an aldehyde of the formula $R^1$—CHO in the presence of a base and a catalytic amount of a thiazolium halide, or in which the derivative of the formula II is converted into a derivative of the formula III

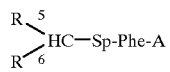
(III)

wherein
$R^5$ is CN and
$R^6$ is NR'R" or OR''', wherein R' and R" in each case independently of one another are alkyl having 1–6 C atoms or phenyl and R''' is $Si(CH_3)_3$, or
$R^5$ and $R^6{}_1$, in each case independently of one another, are SR', or together are $S(CH_2)_nS$, where n is 2, 3 or 4,
and the derivative is treated with a strong base and reacted with an aldehyde of the formula $R^1$—CHO.

Method I comprises catalytic "pole reversal" with a thiazolium halide in the presence of a base.

3-Alkylbenzothiazolium halides, in particular 3-ethylbenzothiazolium bromide, are preferably used.

The reaction is as a rule carried out in a diluent, preferably an aprotic solvent, in particular an alcohol, such as, for example, methanol, ethanol or isopropanol. Weak bases, in particular primary, secondary or tertiary amines, such as, for example, triethylamine, imidazole or pyridine, are preferably employed as the base.

The reaction can be carried out at temperatures of between 0° C. and the boiling point of the reaction mixture, and is preferably carried out at room temperature.

Method II comprises conversion of the formyl derivatives of the formula II into a derivative of the formula III which contains an acid, benzylic hydrogen atom.

Preferred compounds of the formula III are those wherein $R^1$ and $R^2$ together are $S(CH_2)_nS$, where n is 2 or 3, or wherein $R^5$ is CN and $R^6$ is $OSi(CH_3)_3$ or NR'R".

This compound is obtained in a manner which is known per se by reaction of the formyl derivative of the formula III
a) with an alkanedithiol under dehydrating conditions,
b) with trimethylsilylcyanide or
c) with a secondary amine and an alkali metal cyamide (sic).

The deprotonation is as a rule effected with a strong base, preferably with n-butyllithium or lithium diisopropylamide.

The resulting adduct of the formula IV

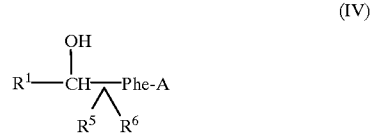
(IV)

is hydrolyzed by a method which is known se (sic), that is to say with dilute acid, if appropriate in the presence of heavy metal salts, such as, for example, mercury, copper or salts of silver (sic).

The aldehydes of the formula II are known (for example DE 28 11 041) or are prepared by known methods.

The derivatives of the formula III and IV (sic) are new and the invention likewise relates to them.

The compounds of the formula I wherein A is a radial of the formula (e) are obtained, for example, by a process in which an α-hydroxyketoalkyl phenol or -aniline derivative of the formula V

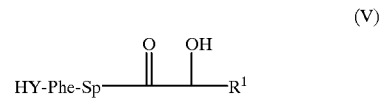
(V)

wherein Phe, $R^1$, Sp and Y have the meaning given, is reacted with cyanuric chloride.

If the reaction is carried out at low temperatures, that is to say between –40° C. and 80° C., preferably 0° C. and 60° C., in particular between 0° C. and room temperature, if appropriate in the presence of a weak base, with only about 1 mol of the compound of the formula II per mol of cyanuric chloride, a triazine derivative of the formula VI

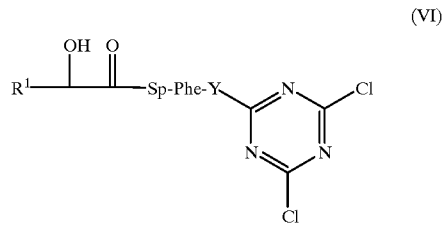
(VI)

wherein $R^1$, Sp, Phe and Y have the meaning given, is intermediately obtained.

The compound of the formula VI is then reacted with one or two further equivalent(s) of a compound of the formula R⁴-Phe-Y, wherein Y, Phe and R⁴ have the meaning given, originally employed and if appropriate subsequently with an alcohol, alkylamine, aniline or phenol having 1 to 10 C atoms.

If about 2 mol of the compound of the formula R⁴-Phe-YH are reacted with cyanuric chloride at these temperatures, a triazine derivative of the formula VII

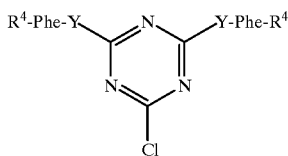

(VII)

wherein R⁴, Phe and Y have the meaning given, is intermediately formed, from which a compound of the formula I (e) is prepared by reaction with about 1 mol of a compound of the formula V.

The compounds of the formula V and VI (sic) are new and the invention likewise relates to them.

The new compounds of the formula V are prepared by a preparation analogous to that for the compounds of the formula I by method 1 or 2, by "pole reversal" of the corresponding hydroxy- or aminobenzaldehyde of the formula

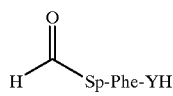

and reaction with an aldehyde of the formula R¹—CHO.

The compounds of the formula I wherein A is a radical of the formula (c) are preferably obtained by a Claisen condensation of an ester of the formula VIII

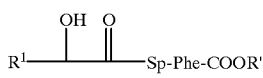

(VIII)

with an acetophenone derivative of the formula IX

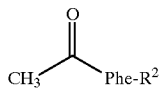

(IX)

for example in accordance with B. R. Hauser et al. Organic Reactions Volume VIII, page 5% (sic), John Wiley and Sons Inc. New York 1954.

The compounds of the formula VIII are likewise new and the invention relates to them, and they can be prepared by a method analogous to method 1 or 2 from formylbenzoic acid esters.

The invention also relates to the process for the preparation of the new compounds of the formula I.

The invention furthermore relates to a cosmetic formulation which comprises an active amount of at least one derivative of the above formula I in a cosmetically compatible carrier.

Those cosmetic formulations wherein the carrier has at least one fatty phase and, in the compound of the formula I,
X is H, and those wherein the carrier contains at least one aqueous phase and X is $SO_3H$ are particularly preferred.

The cosmetic agent according to the invention can be used as an agent for protection of the human epidermis or hair or as a sunscreen agent.

The invention furthermore relates to a method for protection of the skin and natural or sensitized hair from solar rays, an active amount of at least one compound of the formula I being applied to the skin or hair.

"Sensitized hair" means hair which has been subjected to permanent wave treatment or a coloring or bleaching process.

The invention furthermore relates to a colored or non-colored light-stabilized cosmetic formulation which comprises an active amount of at least one benzylidene-camphor derivative of the above formula I.

If the cosmetic agent according to the invention is used as an agent for protection of the human epidermis against UV rays, it is present in various forms usually used for this type. It can thus be, in particular, in the form of oily or oily-alcoholic lotions, emulsions, such as a cream or as a milk in the form of oily-alcoholic, oily-aqueous or aqueous-alcoholic gels or as solid sticks, or can be made up as an aerosol.

It can comprise cosmetic adjuvants which are usually used in this type of agent, such as, for example, thickening agents, softening agents, moisturizing agents, surface-active agents, preservatives, agents which prevent foam formation, perfumes, waxes, lanolin, propellants, dyestuffs and/or pigments, which color the agent itself or the skin, and other ingredients usually used in cosmetics.

The cosmetic agent for protection of the human epidermis as a rule comprises the compound of the formula I in an amount of 0.5 to 10%, based on its total weight.

An oil, wax or other fatty substance, a lower monoalcohol or a lower polyol or mixtures thereof can be used as solubilizing agents. Particularly preferred monoalcohols or polyols include ethanol, i-propanol, propylene glycol, glycerol and sorbitol.

A preferred embodiment of the invention is an emulsion which is in the form as a protective cream or milk and comprises, in addition to the compound of the formula I, fatty alcohols, fatty acid esters, in particular triglycerides of fatty acids, fatty acids, lanolin, naturally occurring or synthetic oils or waxes and emulsifiers in the presence of water.

Other preferred embodiments are oily lotions based on naturally occurring or synthetic oils and waxes, lanolin or fatty acid esters, in particular triglycerides of fatty acids, or oily-alcoholic lotions based on a lower alcohol, such as ethanol, or on a glycol, such as propylene glycol, and/or on a polyol, such as glycerol, and oils, waxes and fatty acid esters, such as triglycerides of fatty acids.

The cosmetic agent according to the invention can also be in the form of an alcoholic gel which comprises one or more lower alcohols or polyols, such as ethanol, propylene glycol or glycerol, and a thickening agent, such as silica. The oily-alcoholic gels furthermore comprise naturally occurring or synthetic oil or wax.

The solid sticks comprise naturally occurring or synthetic waxes and oils, fatty alcohols, fatty acid esters, lanolin and other fatty substances.

The invention also relates to cosmetic sunscreen agents which comprise at least one compound of the formula I and can comprise other UVB and/or UVA filters.

In this case, the amount of the filter of the formula I is as a rule between 1.0 and 8.0% by weight, based on the total weight of the sunscreen agent.

If an agent is made up as an aerosol, the customary propellants, such as alkanes, fluoroalkanes and chlorofluoroalkanes, are as a rule used.

If the agent according to the invention is to protect natural or sensitized hair from UV rays, it can be in the form of a shampoo, lotion, gel or emulsion for rinsing out, the particular formulation being applied before or after shampooing, before or after coloring or bleaching or before or after a permanent wave; or the agent is in the form of a lotion or gel for styling and treatment, as a lotion or gel for brushing or setting a water-wave or in the form of a hair spray, permanent wave or coloring or bleaching agent for the hair. In addition to the compound according to the invention, this agent can comprise adjuvants used in this type of agent, such as surface-active agents, thickening agents, polymers, softening agents, preservatives, foam stabilizers, electrolytes, organic solvents, silicone derivatives, oils, waxes, antiseborrheic agents, dyestuffs and/or pigments which color the agent itself or the hair or other ingredients usually used for hair care. The agent as a rule comprises 1.0 to 5.0% by weight of the compound of the formula I.

The present invention also relates to cosmetic agents which comprise at least one compound of the formula I as agents for protection from UV rays and as antioxidants; these agents comprise hair products, such as hair sprays, waterwave lotions for setting the hair, if appropriate for treatment or gentler styling, shampoos, coloring shampoos, hair coloring agents, makeup products, such as nail varnish, creams and oils for skin treatment, make-up (foundation), lipsticks, skin care agents, such as bath oils or creams, and other cosmetic agents which may cause problems with photostability and/or oxidation in the course of storage because of their components. Such agents as a rule comprise 1.0 to 5.0% by weight of a compound of the formula I.

The invention furthermore relates to a process for protection of cosmetic agents from UV rays and oxidation, an active amount of at least one compound of the formula I being added to these agents.

The invention furthermore relates to the use of the compounds of the formula I as solar filters of a wide absorption range in a wavelength range from 320 to 400 nm.

The invention furthermore relates to the use of the compounds of the formula I as cosmetic products.

As already mentioned above, in the course of its studies, the Applicant Company furthermore has found that the compounds of the formula I exhibit a significant pharmacological activity in the field of preventive treatment of inflammations and skin allergies.

The invention also relates to the compounds of the formula for use as a medicament.

The invention furthermore relates to a pharmaceutical agent which comprises an active amount of at least one compound of the formula I as an active compound in a non-toxic carrier or excipient.

The pharmaceutical agent according to the invention can be administered orally or topically.

For oral administration, the pharmaceutical agent is in the form of lozenges, gelatin capsules or coated capsules, or in the form of a syrup, suspension, solution, emulsion and the like. For topical administration, it is in the form of an ointment, cream, pomade, solution, lotion, gel, spray, suspension and the like.

This agent can comprise inert or pharmaco-dynamically active additives, in particular hydrating agents, antibiotics, steroid or non-steroid anti-inflammatory agents, carotinoids and agents against psoriasis.

This agent can also comprise flavor-improving agents, preservatives, stabilizers, moisture regulators, pH regulators, osmotic pressure modifiers, emulsifiers, local anesthetics, buffers and the like.

It can furthermore be conditioned, in a manner which is known per se, in a sustained release form or in a form in which the active compound is released rapidly.

The following examples are representative for the present invention.

It is assumed that the expert can utilize the above description in the broadest scope even without being given further details. The preferred embodiments are therefore to be interpreted merely as a descriptive disclosure and in no way as a disclosure which is in any way limiting.

The complete disclosure of all the applications, patents and publications listed above and below and the corresponding Application P 42 04 651 filed on Feb. 15, 1992 are introduced into this application by reference.

EXAMPLE 1

3-(4'-(2"-Hydroxy-1"-oxo-ethyl) -benzylidene) -camphor 0.8 g (3.5 mmol) of 3-ethyl-benzothiazolium bromide and triethylamine are added to a reaction mixture of 10 g (35 mmol) of 3-(4'-formylbenzylidene)-camphor (prepared, for example, in accordance with DE 2811041) and 1.2 g of paraformaldehyde in 70 ml of ethanol and the mixture is heated under reflux. When the reaction has ended, the mixture is concentrated and the residue is taken up in ethyl acetate and washed with water. Purification is carried out by means of column chromatography.

Yellow crystals having a melting point of 98° C. are formed. The spectra correspond to the expected compound. UV (ethanol, c=1 mg/100 ml): $\lambda_{max}$=305, E=1(d=1 cm)
Solubility: 5% in Miglyol The following are prepared analogously:
3-(3'-(2"-hydroxy-1"-oxoethyl)-benzylidene)-camphor
3-(4'-(2"-hydrox-1"-oxoethyl)-2 ', 5'-dimethoxy-benzylidene)-camphor (sic)
3-(4'-(2"-hydroxy-1"-oxopropyl)-benzylidene)-camphor
3-(3'-(2"-hydroxy-1"-oxopropyl)-benzylidene)-camphor
3-(4'-(2"-hydroxy-1"-oxobutyl)-benzylidene)-camphor
3-(4'-(2"-hydroxy-1"-oxobutyl) -benzylidene)-camphor (sic).

EXAMPLE 2

2A 4- (Propenylcarboxylic acid ethyl ester) -benzaldehyde diethyl acetal 0.5 mol of ethyl acetate is added to 0.25 mol of sodium ethylate in 100 ml of toluene at 0° C. 0.2 ml of terephthalaldehyde diethyl acetal is slowly added drop-wise and the mixture is subsequently stirred until the reaction is complete. After working up and purification by means of column chromatography, 5 g of the compound 2A are obtained (yield: 63%).

2B Ethyl formylcinnamate

These 35 g (0.12 mol) of compound 2A are dissolved in 300 ml of dioxane and the solution is stirred in the presence of 2 g of Amberlyst 15 at 20° C. Working up leads to 23 g (91%) of ethyl formylcinnamate.

2C Ethyl 4-(2'-hydroxy-1'-oxo-ethyl)-cinnamate 2.7 g (0.011 mol) of 3-ethyl-benzothiazolium bromide and triethylamine are added to a reaction mixture of 23 g (0.11 mol) of ethyl formylcinnamate 2B and 3.8 g of paraformaldehyde in 200 ml of ethanol and the mixture is heated under reflux. After working up and crystallization, white crystals having a melting point of 127° C. are obtained.

The spectra correspond to the expected compound. UV (ethanol, c=1 mg/100 ml): $\lambda_{max}$=293 nm, E=1.35

The following are prepared analogously:
propyl 4-(2'-hydroxy-1'-oxoethyl)-cinnamate
hexyl 4-(2'-hydroxy-1'-oxoethyl)-cinnamate
2-ethylhexyl 4-(2'-hydroxy-1'-oxoethyl)-cinnamate.

EXAMPLE 3

0.8 g (3.5 mmol) of 3-ethylbenzothiazolium bromide and triethylamine are added to a mixture of 35 mmol of 9-(4'-formylbenzylidene)-8-ketotricyclo-[5.2.1.0$^{2.6}$] decane (prepared from 8-ketotricyclo-[5. 2.1.0$^{2.6}$] decane and terephthaldehyde di ethyl acetal (sic) in the presence of sodium methylate and subsequent acetal cleavage) and 1.2 g of paraformaldehyde in 70 ml of ethanol, and the mixture is heated under reflux. After working up analogously to Example 1, 9-(4'-(2"-hydroxy-1"-oxoethyl)-benzylidene)-8-ketotricyclo[5.2.1. 0$^{2.6}$]-decane is obtained. The spectra correspond to the expected compound.

The following are prepared analogously:
9-(4'-(2"-hydroxy-1"-oxopropyl)-benzylidene-8-ketotricyclo[5.2.1.0$^{2.6}$] decane.
9-(4'-(2"-hydroxy-1"-oxobutyl) -benzylidene-8-ketotricyclo [5.2.1.0$^{2.6}$] decane.

Use Examples

| A | Sunscreen cream (water-in-oil) | | % |
|---|---|---|---|
| A | 3-(4'-(2"-Hydroxy-1"-oxoethyl)-benzylidene-camphor | (1) | 2.50 |
|   | Arlacel 481 | (2) | 6.50 |
|   | Arlacel 989 | (2) | 3.50 |
|   | Cetiol A | (4) | 2.00 |
|   | Paraffin oil, viscous (Art. No. 7160) | (1) | 17.00 |
|   | Paraffin, non-caking (Art. No. 7158) | (1) | 3.00 |
|   | Miglyol 812 | (3) | 12.00 |
| B | Karion F liquid (Art. No. 2993) | (1) | 3.00 |
|   | Preservative | | q.s. |
|   | Water, demineralized | | to 100.00 |

Preparation

Heat phases A and B to 75° C. Stir phase B and (sic) into phase A. Homogenize. Cool, while stirring.

Sources of Supply
(1) E. Merck, Darmstadt
(2) ICI, Essen
(3) Hüls Troisdorf AG, Witten
(4) Henkel, Düsseldorf

| B | Sunscreen cream (water-in-oil) | | % |
|---|---|---|---|
| A | Ethyl 4-(2'-hydroxy-1"-oxoethyl)-cinnamate | (1) | 2.50 |
|   | Arlacel 481 | (2) | 6.50 |
|   | Arlacel 989 | (2) | 3.50 |
|   | Cetiol A | (4) | 2.00 |
|   | Paraffin oil, viscous (Art. No. 7160) | (1) | 17.00 |
|   | Paraffin, non-caking (Art. No. 7158) | (1) | 3.00 |
|   | Miglyol 812 | (3) | 12.00 |
| B | Karion F liquid (Art. No. 2993) | (1) | 3.00 |
|   | Preservative | | q.s. |
|   | Water, demineralized | | to 100.00 |

Preparation

Heat phases A and B to 75° C. Stir phase B and (sic) into phase A. Homogenize. Cool, while stirring.

C Investigation of the adhesion to skin

A certain amount of UV filter to be investigated: A=3-(4'-(2"-hydroxy-1"-oxoethyl)-benzylidene)-camphor B=ethyl 4-(2'-hydroxy-1'-oxoethyl)-cinnamate is applied to a sheet of gelatin and, after an appropriate reaction time, the non-bonded UV filter is taken up in ethanol and its amount is determined by UV spectroscopy.

The results obtained by this procedure can be seen from Table I:

| UV filter | Amount (mg) | Reaction time | Amount in ETOH (sic) | in gelatine | Adhesion % |
|---|---|---|---|---|---|
| A | 2 | 10 min | 0.33 | 1.53 | 83 |
| A | 2 | 30 min | 0.53 | 1.23 | 74 |
| A | 2 | 60 min | 0.29 | 1.58 | 86 |
| A | 2 | 17 hrs | 0.56 | 1.28 | 72 |
| A | 20 | 19 hrs | 16.3 | 1.48 | 18.5 |
| B | 0.5 | 3 days | 0.3 | 0.2 | 40 |
| B | 1.0 | 4 days | 0.52 | 0.48 | 48 |

| D | Sunscreen cream (water-in-oil) | | |
|---|---|---|---|
| A | 3-(4'-(2"-Hydroxy-1"-oxoethyl)-benzylidene)-camphor | (1) | 3.0% |
|   | Eusolex 6300 Art No. 5385 | (1) | 3.0% |
|   | Arlacel 481 | (2) | 6.5% |
|   | Arlacel 989 | (2) | 3.5% |
|   | Cetiol A | (3) | 2.0% |
|   | Paraffin oil, viscous Art. No. 7160 | (1) | 17.0% |
|   | Paraffin, non-caking Art. No. 7158 | (1) | 3.0% |
|   | Migliol (sic) 812 | (4) | 12.0% |
| B | Karion F liquid Art. No. 2993 | (1) | 3.0% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.

Sources of Supply
(1) E. Merck, Darmstadt
(2) ICI, Essen
(3) Henkel, Düsseldorf
(4) Hüls Troisdorf AG, Witten

| E | Sunscreen milk (water-in-oil) | | |
|---|---|---|---|
| A | 3-(4'-(2"-Hydroxy-1"-oxoethyl)-benzylidene)-camphor | (1) | 3.0% |
|   | Arlacel 481 | (2) | 3.2% |
|   | Arlacel 989 | (2) | 3.8% |
|   | Paraffin oil highly liquid, Art. No. 7174 | (1) | 16.0% |
|   | Isopropyl myristate | (3) | 3.5% |
|   | Migliol (sic) 812 | (4) | 3.5% |
| B | Propane-1,2-diol Art. No. 7478 | (1) | 3.5% |
|   | Magnesium sulfate heptahydrate Art. No. 5882 | (1) | 0.7% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.

Sources of Supply (1) E. Merck, Darmstadt
(2) ICI, Essen (3) Henkel, Düsseldorf
(4) Hüls Troisdorf AG, Witten

| F | Sunscreen milk (water-in-oil) | | |
|---|---|---|---|
| A | 3-(4'-(2''-Hydroxy-1''-oxoethyl)-benzylidene)-camphor | (1) | 3.0% |
|   | Eusolex 6300 Art. No. 5385 | (1) | 3.0% |
|   | Arlacel 481 | (2) | 3.2% |
|   | Arlacel 989 | (2) | 3.8% |
|   | Paraffin oil, highly liquid, Art. No. 7174 | (1) | 16.0% |
|   | Isopropyl myristate | (3) | 3.5% |
|   | Migliol (sic) 812 | (4) | 3.5% |
| B | Propane-1,2-diol Art. No. 7478 | (1) | 3.5% |
|   | Magnesium sulfate heptahydrate Art. No. 5882 | (1) | 0.7% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.
Sources of Supply
(1) E. Merck, Darmstadt
(2) ICI, Essen
(3) Henkel, Düsseldorf
(4) Hüls Troisdorf AG, Witten

| G | Sunscreen cream (water-in-oil) | | |
|---|---|---|---|
| A | 3-(4'-(2''-Hydroxy-1''-oxoethyl)-benzylidene)-camphor | (1) | 3.0% |
|   | Emulsifier E 2155 | (2) | 8.0% |
|   | Paraffin oil, liquid Art. No. 7162 | (1) | 12.0% |
|   | Paraffin, non-caking Art. No. 7158 | (1) | 2.0% |
|   | Isopropyl myristate | (3) | 3.0% |
|   | Migliol (sic) 812 | (4) | 2.0% |
| B | Propane-1,2-diol Art. No. 7478 | (1) | 4.0% |
|   | Karion F, liquid Art. No. 2993 | (1) | 3.0% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.
Sources of supply:
(1) E. Merck, Darmstadt
(2) ICI, Essen
(3) Henkel, Düsseldorf
(4) Hüls Troisdorf AG, Witten

| H | Sunscreen cream (water-in-oil) | | |
|---|---|---|---|
| A | 3-(4'-(2''-Hydroxy-1''-oxoethyl)-benzylidene)-camphor | (1) | 3.0% |
|   | Eusolex 6300 | (1) | 3.0% |
|   | Emulsifier E 2155 | (2) | 8.0% |
|   | Paraffin oil, liquid Art. No. 7162 | (1) | 12.0% |
|   | Paraffin, non-caking Art. No. 7158 | (1) | 2.0% |
|   | Isopropyl myristate | (3) | 3.0% |
|   | Migliol (sic) 812 | (4) | 2.0% |
| B | Propane-1,2-diol Art. No. 7478 | (1) | 4.0% |
|   | Karion F, liquid Art. No. 2993 | (1) | 3.0% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.
Sources of Supply
(1) E. Merck, Darmstadt
(2) ICI, Essen
(3) Henkel, Düsseldorf
(4) Hüls Troisdorf AG, Witten

| I | Sunscreen milk (water-in-oil) | | |
|---|---|---|---|
| A | 3-(4'-(2''-Hydroxy-1''-oxoethyl) benzylidene)-camphor | (1) | 3.0% |
|   | Arlatone 983 S | (2) | 1.5% |
|   | Arlatone 983 | (2) | 2.2% |
|   | Brij 76 | (2) | 1.5% |
|   | Paraffin oil, liquid Art. No. 7162 | (1) | 5.0% |
|   | Migliol (six) 812 | (3) | 5.0% |
| B | Propane-1,2-diol Art. No. 7478 | (1) | 2.5% |
|   | Karion F, liquid Art. No. 2993 | (1) | 2.5% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.
Sources of Supply
(1) E. Merck, Darmstadt
(2) ICI, Essen
(3) Hüls Troisdorf AG, Witten

| J | Sunscreen milk (water-in-oil) | | |
|---|---|---|---|
| A | 3-(4'-(2''-Hydroxy-1''-oxoethyl)-benzylidene)-camphor | (1) | 3.0% |
|   | Eusolex 6300 Art. No. 5385 | (1) | 3.0% |
|   | Arlatone 983 S | (2) | 1.5% |
|   | Arlatone 983 | (2) | 2.2% |
|   | Brij 76 | (2) | 1.5% |
|   | Paraffin oil, liquid Art. No. 7162 | (1) | 5.0% |
|   | Migliol (sic) 812 | (3) | 5.0% |
| B | Propane-1,2-diol Art. No. 7478 | (1) | 2.5% |
|   | Karion F, liquid Art. No. 2993 | (1) | 2.5% |
|   | Preservative | (1) | q.s. |
|   | Water, demineralized | | to 100% |

Phase A is heated to 75° C. and phase B is heated to 80° C. Phase B is stirred slowly into phase A and the mixture is homogenized.
Sources of Supply
(1) E. Merck, Darmstadt
(2) ICI, Essen
(3) Hüls Troisdorf AG, Witten

We claim:
1. An α-hydroxyketoalkyl derivative of the formula I

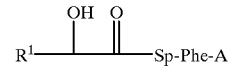

wherein $R^1$ is H or alkyl having 1 to 10 C atoms,

Sp is $(CH_2)_n$ or —CH═CH—, n is 0 or an integer between 1 and 10,

Phe is phenylene which is unsubstituted or substituted by 1 to 4 hydroxyl, alkyl or alkyloxy groups, the alkyl groups in each case having 1–10 C atoms, and A is a substituent group which has a total of up to 60 carbon, sulfur, nitrogen and oxygen atoms in the basic structure and contains a conjugated π-electron system of at least 4

π-electrons in conjugation, wherein A is not of formula (b)

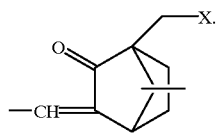
(b)

2. A method of using α-hydroxyketoalkyl derivatives as light protection filters which comprises preparing cosmetic or pharmaceutical products with an α-hydroxyketoalkyl derivative, characterized in that the α-hydroxyketoalkyl derivative is of the formula I

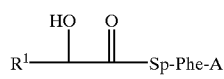
I wherein
$R^1$ is H or alkyl having 1 to 10 C atoms,
Sp is $(CH_2)_n$ or —CH=CH—,
n is 0 or an integer between 1 and 10,
Phe is phenylene which is unsubstituted or substituted by 1 to 4 hydroxyl, alkyl or alkyloxy groups, the alkyl groups in each case having 1–10 C atoms, and
A is a radical chosen from the formulae (a) and (c) to (g):

—CH=CH—COOR$^2$
(a)

(c)

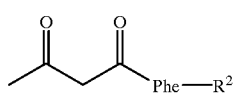
(d)

(e)

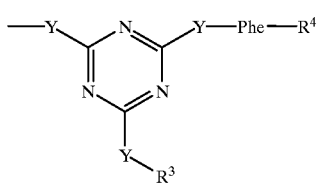
(f)

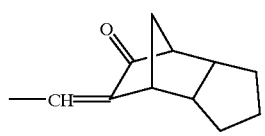
(g)

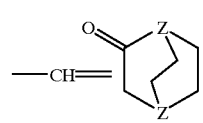

wherein, in each case independently of one another,
$R^2$ has one of the meanings given for $R^1$.

Phe has the meaning given above,
X is H, $R^2$ or $SO_3H$,
m is 0, 1, 2 or 3,
Y in each case independently of one another is O or NH,
Z in each case independently of one another is CH or N and
$R^3$ has one of the meanings of $R^1$ or is Phe-$R^4$, wherein $R^4$ is a radical chosen from the formula (a), (d), (f) and (g).

3. A method of using α-hydroxyketoalkyl derivatives as light protection filters which comprises preparing cosmetic or pharmaceutical products with a α-hydroxyketoalkyl derivative, characterized in that the α-hydroxyketoalkyl derivative is of the formula I

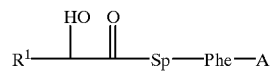
I wherein
$R^1$ is H or alkyl having 1 to 10 C atoms,
Sp is $(CH_2)_n$ or —C=CH—,
n is 0 or an integer between 1 and 10,
Phe is unsubstituted 1,4-phenylene, and
A is a substituent group which has a total of up to 60 carbon, sulfur, nitrogen and oxygen atoms in the basic structure and contains a conjugated π-electron system of at least 4 π-electrons in conjugation with the Phe group, wherein A is not of formula (b)

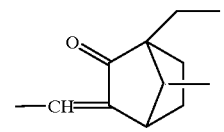
(b)

4. An α-hydroxyketoalkyl derivative of the formula Ia

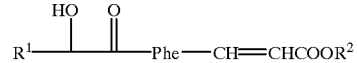
(Ia)

or of the formula Ib

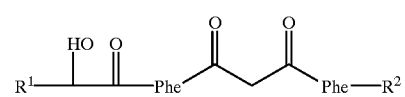
(Ib)

wherein
$R^1$ is H or alkyl having 1 to 10 C atoms,
Phe is phenylene which is unsubstituted or substituted by 1 to 4 hydroxyl, alkyl or alkyloxy groups, the alkyl groups in each case having 1–10 C atoms, and
$R^2$ has one of the meanings given for $R^1$.

5. A process for the preparation of, an α-hydroxyketoalkyl derivative of the formula I

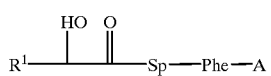

characterized in that a formyl-benzylidene-camphor derivative of the formula II

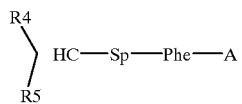

is reacted with an aldehyde of the formula $R^1$—CHO in the presence of a base and a catalytic amount of a thiazolium halide, or in derivative of the formula II is converted into a derivative of the formula III

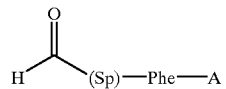

and the derivative is treated with a strong base and reacted with an aldehyde of the formula $R^1$—CHO wherein $R^1$ is H or alkyl having 1 to 10 C atoms, Sp is $(CH_2)_n$ or —CH=CH—, n is 0 or an integer between 1 and 10, $R^4$ is CN and $R^5$ is NR'R" or OR'" wherein R' and R" in each case independently of one another are alkyl having 1–6 C atoms or phenyl and R'" is $Si(CH_3)_3$, or $R^4$ and $R^5$, in each case independently of one another are SR', or together are is $Si(CH_2)_nS$, where n is 2, 3 or 4, Phe is phenylene which is unsubstituted or substituted by 1 to 4 hydroxyl, alkyl or alkyloxy groups, the alkyl groups in each case having 1–10 C atoms, and A is a substituent group which has a total of up to 60 carbon, sulfur, nitrogen and oxygen atoms in the basic structure and contains a conjugated π-electron system of at least π-electrons in conjugation with the Phe group, wherein A is not of formula (b)

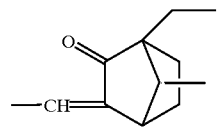

* * * * *